United States Patent [19]
Neely et al.

[11] Patent Number: 5,610,528
[45] Date of Patent: Mar. 11, 1997

[54] CAPACITIVE BEND SENSOR

[75] Inventors: James S. Neely, Wappingers Falls; Phillip J. Restle, Katonah, both of N.Y.

[73] Assignee: International Business Machines Corporation, Armonk, N.Y.

[21] Appl. No.: 496,236

[22] Filed: Jun. 28, 1995

[51] Int. Cl.$^6$ .............. G01B 7/30; H01G 5/14; G01R 27/26
[52] U.S. Cl. .......... 324/660; 324/686; 324/71.1; 33/1 N; 361/278; 361/292; 361/296
[58] Field of Search .................. 324/658, 660, 324/681, 686, 687, 690, 71.1; 33/1 N, 1 PT, 534; 361/278, 292, 296

[56] References Cited

U.S. PATENT DOCUMENTS

| | | | |
|---|---|---|---|
| 3,723,866 | 3/1973 | Michaud et al. | 324/61 R |
| 4,743,902 | 5/1988 | Andermo | 340/870.37 |
| 4,810,951 | 3/1989 | Meyer | 324/61 R |
| 4,940,063 | 7/1990 | Challis | 33/534 X |
| 4,941,363 | 7/1990 | Doemens et al. | 361/290 X |
| 4,977,811 | 12/1990 | Suzuki et al. | 33/1 PT X |
| 5,023,559 | 6/1991 | Andermo | 324/662 |
| 5,055,838 | 10/1991 | Wise et al. | 340/870.37 |
| 5,237,284 | 8/1993 | VanDerValk | 324/662 |
| 5,304,937 | 4/1994 | Meyer | 324/686 |
| 5,313,840 | 5/1994 | Chen et al. | 73/763 |

*Primary Examiner*—Kenneth A. Wieder
*Assistant Examiner*—Glenn W. Brown
*Attorney, Agent, or Firm*—Jay P. Sbrollini

[57] ABSTRACT

A capacitive bend sensor includes a first element having a comb-patterned portion of conducting material, and a second element having a comb-patterned portion of conducting material. A dielectric material is disposed between the comb-patterned portion of the first element and the comb-patterned portion of the second element. The first element is bonded to the second element such that the comb-patterned portion of the first element slides relative to the comb-patterned portion of the second element when the first and second elements are bent. Bend angle is measured according to the alignment of the comb-patterned portion of the first element and the comb-patterned portion of the second element. The sensor may be coupled to a human finger to measure bend angle of the finger, or may be coupled to a joint of a human body to measure bend angle of the joint.

6 Claims, 4 Drawing Sheets

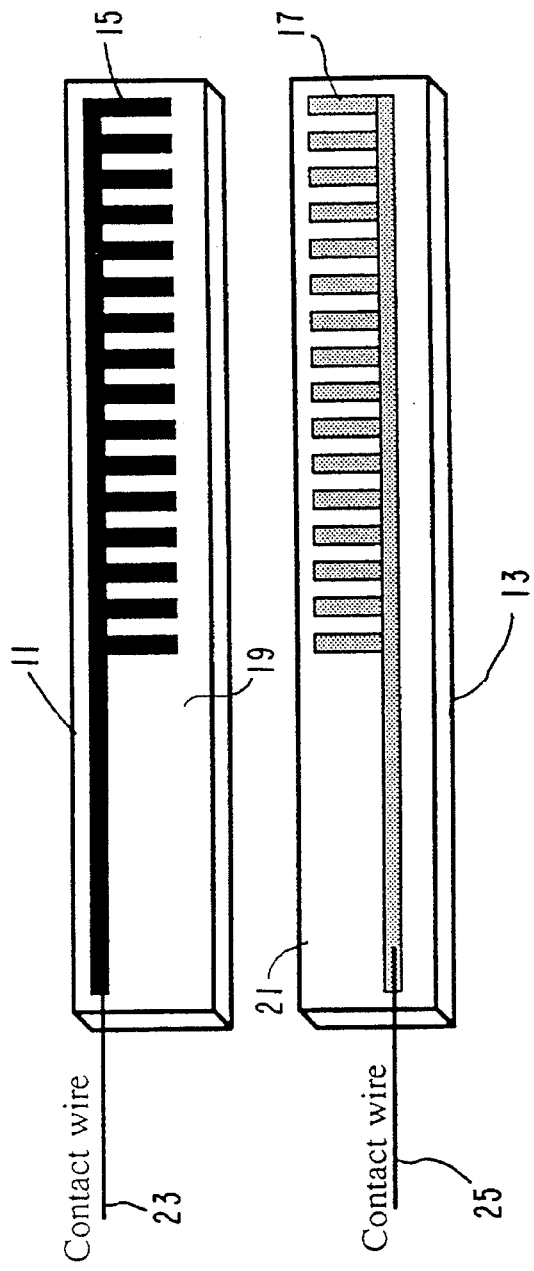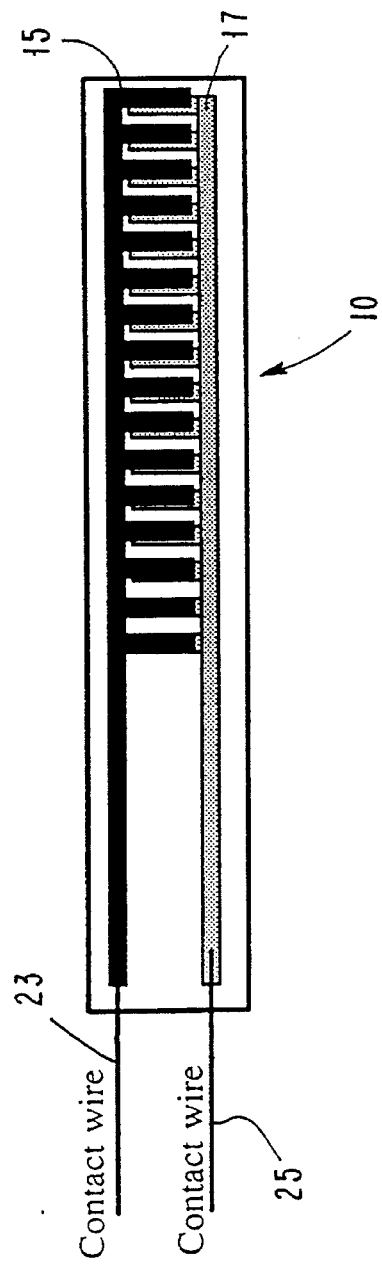
FIG. 1
FIG. 2

CAPACITIVE BEND SENSOR

BACKGROUND OF THE INVENTION

1. Technical Field

The invention relates to capacitive sensors, and, more particularly, to capacitive sensors that measure a bend angle.

2. Description of the Prior Art

Interfaces that sense the position and orientation of the user's fingers, hands, head or other body joints are an integral part of many applications, such as computer game systems, virtual keyboards, interactive visualization, and three-dimensional graphics systems.

In existing systems, three-dimensional position sensors, such as those manufactured by Polhemus Corp., are typically affixed to the user's body parts (i.e. hands and head) to determine the position of the user's respective body parts. In addition, the user typically wears gloves that include bend angle sensors that measure the bend angle of the user's fingers. Bend angle sensors developed to date have either been inexpensive yet inaccurate, or accurate and very expensive.

For example, Mattel manufactures an inexpensive hand-position-interface glove that uses a flexible resistor whose resistance changes with bending. This technique has limited bend angle sensitivity and reproducibility. In another example, VPL Research Inc. has developed an expensive hand position interface glove that measures finger bend angle by sensing the loss of light from bent optical fibers. This sensing technique gives no information about the direction of the bend, only its magnitude.

Thus, there is a need in the art to provide an accurate yet inexpensive means of sensing the bend angle of fingers and other body parts. More particularly, there is a need to provide a sensor for measuring "backwards" bending (for example, the bending of the wrists "up and down"), and for measuring perpendicular planes of bending (for example, a first plane characterized by the "up" and "down" bending of the thumb or wrist and a second plane characterized by the "sideways" bending of the thumb or wrist).

SUMMARY OF THE INVENTION

The above-stated problems and related problems of the prior art are solved with the principles of the present invention, a capacitive bend sensor that includes a first element having a comb-patterned portion of conducting material, and a second element having a comb-patterned portion of conducting material. A dielectric material is disposed between the comb-patterned portion of the first element and the comb-patterned portion of the second element. The first element is bonded to the second element such that the comb-patterned portion of the first element slides relative to the comb-patterned portion of the second element when the first and second elements are bent. Bend angle is measured according to the alignment of the comb-patterned portion of the first element and the comb-patterned portion of the second element.

The sensor may be coupled to a human finger to measure bend angle of the finger, or may be coupled to a joint of a human body to measure bend angle of the joint.

BRIEF DESCRIPTION OF THE DRAWINGS

FIG. 1 is a pictorial representation of the two conducting strips of the capacitive bend-angle sensor of the present invention prior to assembly;

FIG. 2 is a top view of the capacitive bend-angle sensor of the present invention; the slight mis-alignment of the combs near one end is due to a slight bending of the sensor parallel to the page, and perpendicular to the long axis of the sensor;

DETAILED DESCRIPTION OF THE PREFERRED EMBODIMENTS

According to the present invention, the bend angle of one or more of the user's joints is measured by a capacitive sensor 10. As shown in FIG. 1, the capacitive sensor includes at least two elements 11,13 that consist of a flexible, electrically insulating material such as plastic. One surface of each element has a comb pattern 15,17 of conducting material, such as a metal film or conducting polymer, and a dielectric layer 19,21 covering the comb material.

Figure 3:
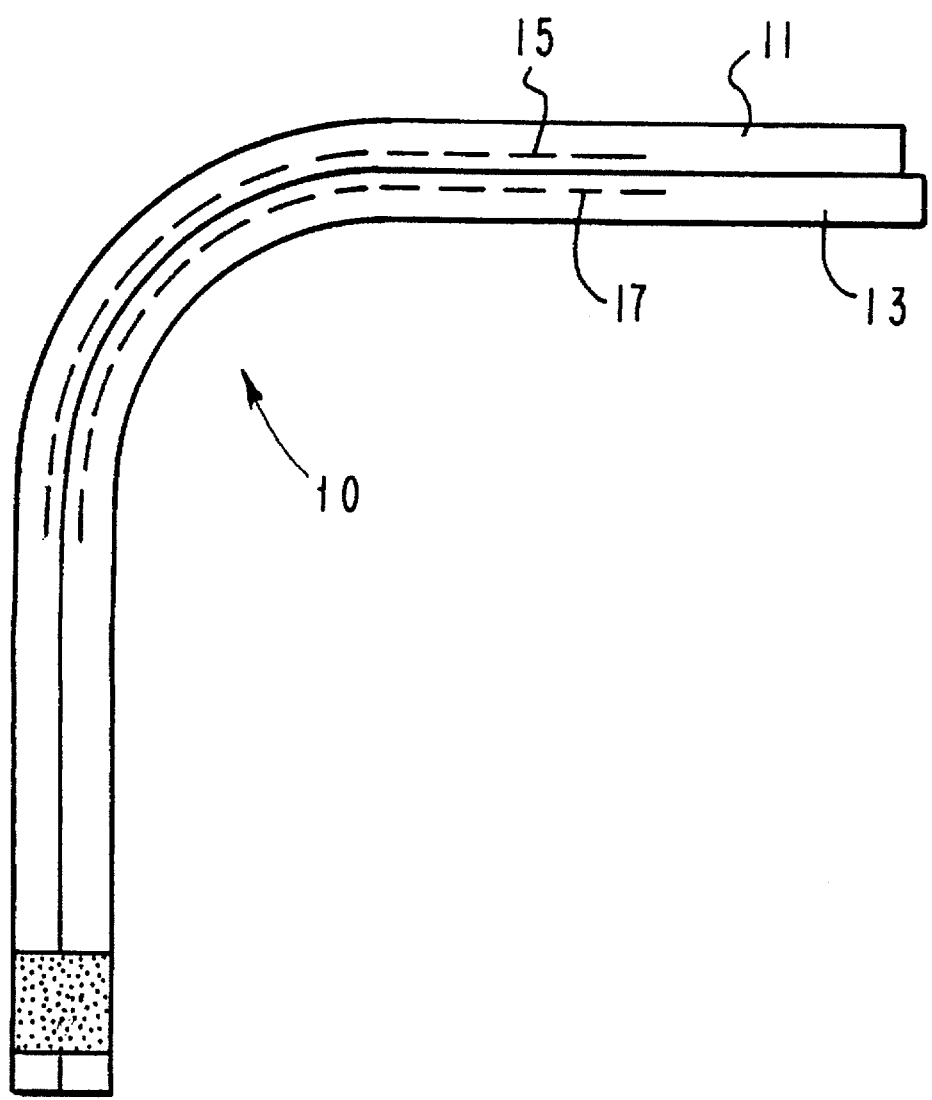
FIG. 3 is a side view of the capacitive bend-angle sensor of the present invention; shown with a 90° bend.

As shown in FIG. 2, to measure bend angle, the two elements 11,13 are placed together such that the two comb patterns 15,17 are in close proximity, separated only by one or more dielectric layers. The two elements 11,13 are then bonded together. Preferably, the comb patterns 15,17 of each of the elements 11,13 are disposed near one end of the elements, and the elements are bonded together on the opposite end as shown in FIG. 3. Electrical contacts 23,25 (wires) are affixed to the conducting comb patterns 15,17. The two elements 11,13 may be placed in flexible plastic tubing (not shown) or other structure that contains and protects the two elements 11,13, and keeps them pressed together.

As shown in FIG. 3, when the sensor 10 is bent around an axis A (perpendicular to the plane of the figure, the two flexible elements 11,13 slide relative to one another, except at the end where they are bonded together. When the two conducting combs 15,17 slide relative to one another, the capacitance changes from a maximum when the conducting teeth of the comb are aligned, to a minimum when the teeth in one comb are aligned with the spaces on the other comb. The capacitance between the two comb patterns is therefore linearly proportional to the bending angle of the sensor for a range of bend angles.

Preferably, the alignment of the comb patterns 15,17 is chosen to be offset at zero bend angle, allowing for both positive and negative bend angles to be distinguished and measured. Moreover, the thicknesses of the dielectric layers, the spacing of the teeth of the combs, and the alignment of the combs at zero bending angle, and the bonding point, are chosen so that the measured capacitance is a linear measurement of bend angle over the desire angle range.

Though initial alignment is done at manufacture to ensure the desired range of bend angles, a more accurate calibration procedure could be performed for each user session, for example, by measuring the sensor response at two or more preset positions. For instance, to calibrate one or more finger sensors, the user could first be prompted to close both hands into fists, and secondly to spread out all fingers as far as possible.

Unlike other measurement techniques, the capacitive bend-angle sensor 10 of the present invention is relatively insensitive to bending or twisting that may be experienced around axes other than the axis of interest. Moreover, separate sensors can be used to measure bending of the same joint about different axes to obtain complete position information.

Figure 6A:
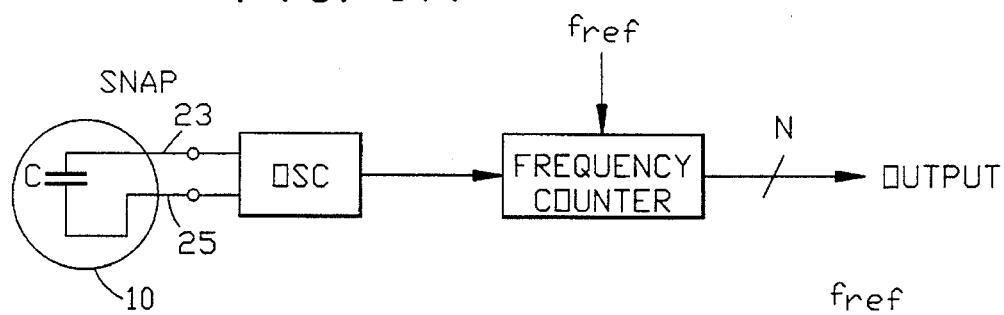
FIGS. 6 (A)–(C) are functional block diagrams of circuitry that interfaces to the sensor of the present invention to produce a digital signal proportional to the bend-angle of the sensor.
Figure 6B:
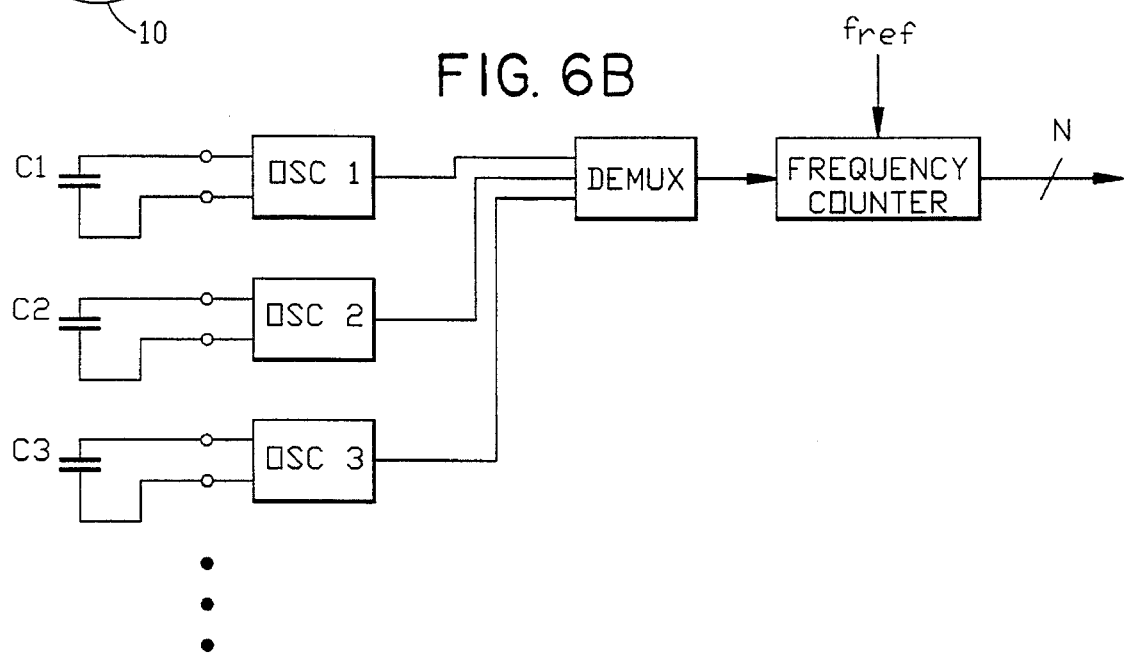
Figure 6C:
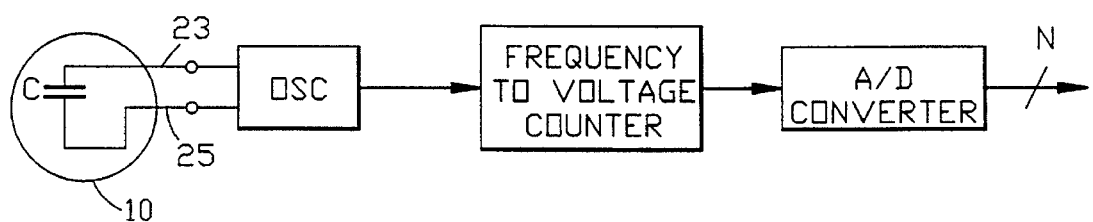

As illustrated in FIG. 6(A), a simple interface circuit consisting of an oscillator and a frequency counter can be utilized to produce a digital signal proportional to the bend-angle of the sensor 10. More particularly, the wire contacts 23,25 of the capacitive sensor 10 are input to relaxation oscillator that generates a signal whose frequency is proportional to the characteristic capacitance C of the sensor 10 as set by the bend-angle of the sensor 10. The output of the relaxation oscillator and a signal having a fixed reference frequency $f_{ref}$, are input to a frequency counter. The reference frequency $f_{ref}$ is preferably much higher than the maximum frequency of the signal output from the relaxation oscillator. The frequency counter outputs a digital signal that represents the relationship between the frequency of the output of the relaxation oscillator and the fixed reference frequency $f_{ref}$, which is thus proportional to the bend-angle of the sensor 10. The digital signal output from the frequency counter may be read periodically to determine the bend-angle of the sensor 10. In addition, as shown in FIG. 6(B), a demultiplexer may be used such that more than one sensor/oscillator pair may be input to the frequency counter, thus reducing the number of components required to measure a bend-angle output from a large number of sensors 10. Moreover, the functions of the frequency counter of FIG. 6(A) can be performed by a frequency-to-voltage-converter and an analog-to-digital converter as shown in FIG. 6(C). The frequency-to-voltage converter may include a voltage controlled oscillator and phase-lock loop.

Figure 4:
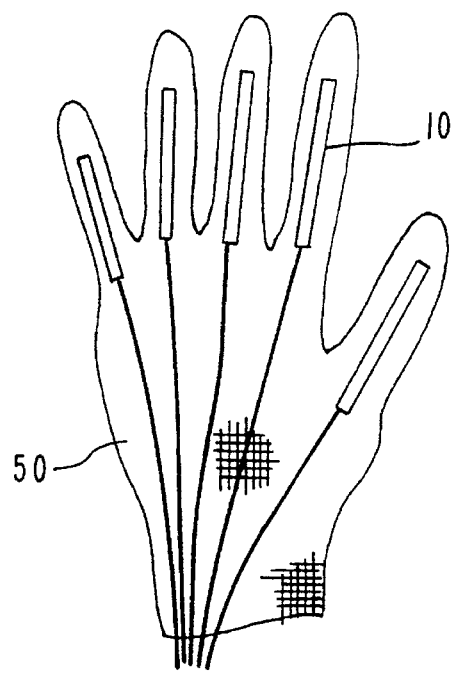
FIG. 4 illustrates the capacitive bend-angle sensor of the present invention attached to a glove to measure the bend-angle of one or more fingers and/or thumb of the human hand.

As shown in FIG. 4, a number of capacitive bend-angle sensors 10 of the present invention can be attached to a glove 50 to measure the bend angle of each finger of a human hand. In addition, a number of the sensors 10 can be used to measure the location of each finger relative to the hand. For example, to measure the location of a finger, three sensors 10 can be used: two sensors 10 may be attached to the glove 50 such that they are disposed above the two primary finger joints, and the third sensor may be attached to the glove 50 such that it is disposed above the base of the finger. In this case, the two sensors measure the curling bend of the two primary joints of the finger and the third sensor measures the horizontal angle of the finger relative to the hand.

Figure 5:
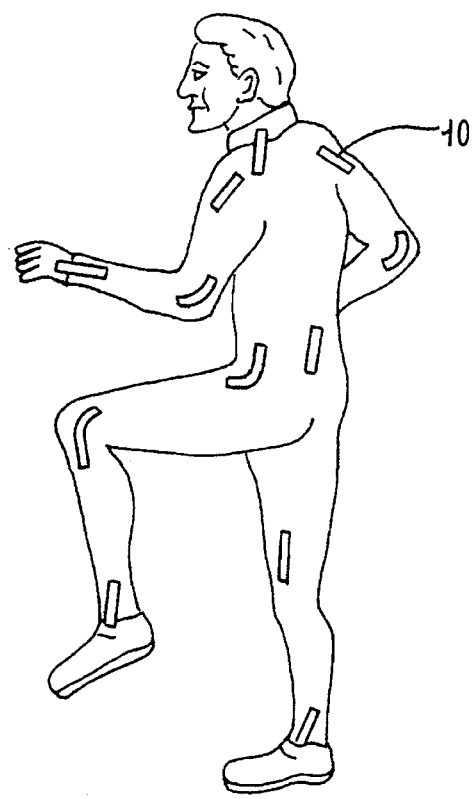
FIG. 5 illustrates the capacitive bend-angle sensor of the present invention attached to a body suit to measure the bend-angle of various joints of the human body.

As shown in FIG. 5, the capacitive bend-angle sensor 10 of the present invention can be utilized to measure the bend angle of any joint on the human body in order to determine the relative position and movement of the limbs of the human body. A single sensor 10 may be sufficient to measure the bending angle of simple bending joints, such as the elbow and knee. However, three sensors may be needed to determine the bending angle(s) of complex bending joints (i.e., those joints that have two or more bend axes), for example, a shoulder or neck. For example, two sensors may be utilized to determine the bend-angles of the human wrist, and a third sensor may be utilized to determine the "twist-ing" of the wrist. To measure the bend angle of the spine, several sensors may be required depending upon the desired resolution. In order to measure the bend angle of the various joints, the sensor may be incorporated into form-fitting clothing such as a body suit, or into portions of clothing such as shirt sleeves.

Applications of this invention include virtual keyboards where finger motions are interpreted as key-presses on an imaginary keyboard, eliminating the need for an actual keyboard, and allowing complete flexibility in the shape and function of the virtual keyboard. This is an example of a wider field of application known as virtual reality. Computer games are another application.

Another field of application is the use of the sensor of the present invention in biofeedback techniques. For example, the sensors of the present invention may be used to measure the bend angle of the spine, and the user notified when correct (or incorrect) posture is achieved. In another example, the sensors of the present invention may be used to objectively monitor physical therapy exercises by measuring flexion and extension with inexpensive, portable, possibly wearable equipment.

Although the invention has been shown and described with respect to the particular embodiment(s) thereof, it should be understood by those skilled in the art that the foregoing and various other changes, omissions, and additions in the form and detail thereof may be made without departing from the spirit and scope of the invention.

We claim:

1. A sensor for measuring bend angle comprising:
   a first element having a comb-patterned portion of conducting material;
   a second element having a comb-patterned portion of conducting material;
   a dielectric material between said comb-patterned portion of said first element and said comb-patterned portion of said second element;
   wherein said first element is bonded to said second element such that said comb-patterned portion of said first element slides relative to said comb-patterned portion of said second element when said first and second elements are bent; and
   wherein said bend angle is measured according to alignment of said comb-patterned portion of said first element and said comb-patterned portion of said second element.

2. The sensor of claim 1, wherein said conducting material is metal.

3. The sensor of claim 1, wherein said conducting material is a conducting polymer.

4. The sensor of claim 1, wherein said first and second elements each have a first end disposed opposite a second end, wherein said first end of said first element is bonded to said first end of said second element, and said comb-patterned portion of said first and second elements are disposed near said second ends of said first and second elements, respectively.

5. The sensor of claim 1, wherein said sensor is coupled to a human finger to measure bend angle of said finger.

6. The sensor of claim 1, wherein said sensor is coupled to a joint of a human body to measure bend angle of said joint.

* * * * *